(12) United States Patent
Mohindra

(10) Patent No.: US 11,008,540 B2
(45) Date of Patent: May 18, 2021

(54) MANUFACTURING FACILITY FOR THE PRODUCTION OF BIOPHARMACEUTICALS

(71) Applicant: Lonza Limited, Visp (CH)

(72) Inventor: Atul Mohindra, Slough (GB)

(73) Assignee: Lonza Ltd., Visp (CH)

( * ) Notice: Subject to any disclaimer, the term of this patent is extended or adjusted under 35 U.S.C. 154(b) by 50 days.

(21) Appl. No.: 15/771,053

(22) PCT Filed: Oct. 26, 2016

(86) PCT No.: PCT/EP2016/075869
§ 371 (c)(1),
(2) Date: Apr. 25, 2018

(87) PCT Pub. No.: WO2017/072201
PCT Pub. Date: May 4, 2017

(65) Prior Publication Data
US 2019/0055508 A1    Feb. 21, 2019

Related U.S. Application Data

(60) Provisional application No. 62/299,930, filed on Feb. 25, 2016, provisional application No. 62/246,478, filed on Oct. 26, 2015.

(51) Int. Cl.
| | |
|---|---|
| *C12M 3/00* | (2006.01) |
| *C12M 1/00* | (2006.01) |
| *B01D 15/36* | (2006.01) |
| *C07K 1/36* | (2006.01) |
| *B01D 61/14* | (2006.01) |
| *B01D 61/18* | (2006.01) |
| *B01D 61/58* | (2006.01) |

(Continued)

(52) U.S. Cl.
CPC .......... *C12M 23/58* (2013.01); *B01D 15/362* (2013.01); *B01D 61/145* (2013.01); *B01D 61/18* (2013.01); *B01D 61/58* (2013.01); *C07K 1/36* (2013.01); *C12M 23/28* (2013.01); *C12M 41/00* (2013.01); *C12M 41/48* (2013.01); *C12M 47/02* (2013.01); *C12M 47/04* (2013.01); *B01D 2311/2623* (2013.01); *B01D 2311/2688* (2013.01); *B01D 2313/13* (2013.01); *B01D 2315/16* (2013.01)

(58) Field of Classification Search
None
See application file for complete search history.

(56) References Cited

U.S. PATENT DOCUMENTS

| | | |
|---|---|---|
| 5,656,491 A | 8/1997 | Cassani et al. |
| 6,395,538 B1 * | 5/2002 | Naughton .............. C12M 41/32 435/288.7 |
| 7,379,783 B2 | 5/2008 | Popp |

(Continued)

FOREIGN PATENT DOCUMENTS

WO    WO 2015/003012 A2    1/2015

OTHER PUBLICATIONS

European Office Action issued in counterpart European Application No. 16791347.4 dated Jun. 11, 2019 (11 pages).

(Continued)

*Primary Examiner* — Nathan A Bowers
(74) *Attorney, Agent, or Firm* — Dority & Manning, P.A.

(57) ABSTRACT

A manufacturing facility for the continuous production of biopharmaceuticals integrated with single-use disposable technology.

40 Claims, 6 Drawing Sheets

(51) Int. Cl.
*C12M 1/34* (2006.01)
*C12M 1/36* (2006.01)

(56) References Cited

U.S. PATENT DOCUMENTS

| | | |
|---|---|---|
| 7,379,784 B2 | 5/2008 | Popp |
| 7,392,107 B2 | 6/2008 | Popp |
| 7,428,442 B2 | 9/2008 | Popp |
| 7,444,197 B2 | 10/2008 | Popp |
| 7,471,991 B2 | 12/2008 | Popp |
| 7,509,185 B2 | 3/2009 | Popp |
| 7,629,167 B2 | 12/2009 | Hodge et al. |
| 7,799,273 B2 | 9/2010 | Popp |
| RE43,527 E | 7/2012 | Popp |
| 8,298,054 B2 | 10/2012 | Hodge et al. |
| 8,491,839 B2 | 7/2013 | Popp |
| 8,591,811 B2 | 11/2013 | Popp |
| 8,660,680 B2 | 2/2014 | Popp |
| 9,008,815 B2 | 4/2015 | Popp |
| 9,092,028 B2 | 7/2015 | Popp |
| 9,195,228 B2 | 11/2015 | Popp |
| 9,304,509 B2 | 4/2016 | Popp |
| 2007/0215534 A1 | 9/2007 | Thommes et al. |
| 2009/0305626 A1 | 12/2009 | Hope |
| 2011/0280797 A1 | 11/2011 | Mohtadi et al. |
| 2012/0077232 A1* | 3/2012 | Budaraju ........ C12M 41/32 435/93 |
| 2012/0077429 A1 | 3/2012 | Wernimont et al. |
| 2013/0005021 A1* | 1/2013 | Bell ........ C12M 29/18 435/252.7 |
| 2013/0280797 A1 | 10/2013 | Rao et al. |
| 2014/0255994 A1* | 9/2014 | Konstantinov ...... B01D 15/327 435/69.6 |
| 2015/0353896 A1* | 12/2015 | Bruninghaus ........ C12M 27/16 435/183 |
| 2016/0041551 A1 | 2/2016 | Popp |
| 2016/0097074 A1 | 4/2016 | Collins et al. |
| 2016/0145563 A1* | 5/2016 | Berteau ........ C12M 23/28 435/325 |
| 2017/0058308 A1* | 3/2017 | Aakesson ........ C12P 21/00 |
| 2017/0107476 A1 | 4/2017 | Polley et al. |
| 2019/0144890 A1* | 5/2019 | Subbian ........ C12P 21/00 435/296.1 |
| 2019/0358633 A1* | 11/2019 | Collins ........ B01L 3/50273 |

OTHER PUBLICATIONS

Klutz et al., "Developing the biofacility of the future based on continuous processing and single-use technology," Journal of Biotechnology, Jun. 16, 2015, pp. 120-130, vol. 213, Elsevier, Amsterdam, NL, XP029284038 (11 pages).
International Search Report (PCT/ISA/210) issued in PCT Application No. PCT/EP2016/075869 dated Apr. 19, 2017 (eight pages).
Written Opinion (PCT/ISA/237) issued in PCT Application No. PCT/EP2016/075869 dated Apr. 19, 2017 (11 pages).
Birch et al., "Antibody production" Advanced Drug Delivery Reviews, Aug. 7, 2006, pp. 671-685, vol. 58, No. 5-6, Elsevier, XP024892148.
Shukla et al., "Recent advances in large-scale production of monoclonal antibodies and related proteins", Trends in Biotechnology, May 1, 2010, pp. 253-261, vol. 28, No. 5, Elsevier Publications, XP027020088.
Marichal-Gallardo et al., "State-of-the-art in downstream processing of monoclonal antibodies: Process trends in design and validation", Biotechnology Progress, Jul. 26, 2012, pp. 899-916, vol. 28, No. 4, XP055153550.
Abhinav et al., "Single-use disposable technologies for biopharmaceutical manufacturing" Trends in Biotechnology, Nov. 21, 2012, pp. 147-154, Elsevier Publications, Cambridge, GB, XP028985934.
Zhou et al., "Implementation of advanced technologies in commercial monoclonal antibody production", Biotechnology Journal, Oct. 1, 2008, pp. 1185-1200, vol. 3, No. 9-10, XP055264944.
Kelley, "Industrialization of mAb production technology: The bioprocessing industry at a crossroads", MABS, Sep. 1, 2009, pp. 443-452, vol. 1, No. 5, XP055344464.
Shukla et al., "Downstream processing of monoclonal antibodies—Application of platform approaches", Journal of Chromatography B: Biomedical Sciences & Applications, Mar. 12, 2007, pp. 28-39, Elsevier, Amsterdam, NL, XP005922825.
Chon et al., "Advances in the production and downstream processing of antibodies", New Biotechnology, Sep. 1, 2011, pp. 458-463, vol. 28, No. 5, XP028290740.
Chinese-language Office Action issued in Chinese Application No. 201680062877.0 dated Apr. 7, 2020 with English translation (17 pages).

\* cited by examiner

FIG. 1 Batch Processing

FIG. 2 Continuous Processing

FIG. 3 Hybrid Processing

FIG. 4 Cell viability using different media

FIG. 6

MANUFACTURING FACILITY FOR THE PRODUCTION OF BIOPHARMACEUTICALS

CROSS REFERENCE TO RELATED APPLICATIONS

This application is a U.S. National Stage Application of International Application No. PCT/EP2016/075869, filed on Oct. 26, 2016, which claims priority to and the benefit of U.S. Provisional Application No. 62/246,478, filed Oct. 26, 2015, and U.S. Provisional Application No. 62/299,930, filed Feb. 25, 2016; all of which are expressly incorporated herein by reference in their entireties.

BACKGROUND OF THE INVENTION

Over the past few decades, the biopharmaceutical industry has made a number of advancements in developing more robust, efficient and cost effective methods for manufacturing biopharmaceuticals in batch mode. These advancements (e.g., expression systems, improved tools to develop and model production processes and adoption of single-use/disposable systems) can also be applied more acutely to current trends related to continuous bioprocesses. Continuous processing or production is a flow production method used to manufacture, produce, or process materials without interruption. Investments in continuous processing in the biopharmaceutical industry have been influenced by a number of business drivers, such as accelerated development times for continuously operated steps, reduced overall costs, maintained stringent quality, regulatory requirements, and increased flexibility to match changing product demands. Other advantages of continuous over batch production include consistent product quality, smaller equipment, streamlined process flow, low process cycle times, steady state operation, and high volumetric productivity.

In the biopharmaceutical industry, the term "single-use" (also commonly known as "disposable") refers to a product that is intended for a one-time use. The adoption of single-use technologies across all steps of biopharmaceutical manufacturing has accelerated in recent years. Today, users can choose from a large selection of single-use products from a range of suppliers. This trend is driven by a number of advantages over stainless steel systems reduced capital investment and operational costs, improved safety, and flexibility, etc., with respect to production scheduling. These advantages drive down contamination rates and enhance the efficiency of a production facility while reducing manufacturing costs (both operational and maintenance).

Single-use options exist for most steps of a protein bio-production process. Such options include process fluid mixing and storage systems, cryopreservation systems, bioreactors (used for both inoculum expansion and production process steps), bulk material and product storage, distribution assemblies and manifolds, sensors, and a number of disposable filtration and chromatography systems. Many of these technologies have already gained wide industry acceptance and furthermore, have been used to manufacture protein products that are approved by the regulatory authorities. For cell therapy manufacturing, plastic dishes and flasks have been used for adherent and non-adherent cell culture and a large proportion of adherent cell-based therapies are currently manufactured in multi-layered plastic flasks. The next generation of cell therapies will be manufactured using bioreactors. For this reason, bioreactor-based cell therapy manufacturing will benefit from utilizing single-use technologies at various, or even all, steps, including, but not limited to, tissue acquisition to final drug product formulation.

In this regard, the strategy is to increase the use of disposable technologies to produce high quality, safe, and cost effective active pharmaceutical ingredients (APIs) and biopharmaceutical products including, but not limited to, recombinant proteins, monoclonal antibodies, protein-drug conjugates, viral based therapeutics and cell therapies. With single-use technologies, it is possible to maintain and increase quality, reliability of supply, throughput, and reduce costs of manufacturing processes. Moreover, the market shows an increase need to develop and implement disposable/single-use technologies for continuous bio-manufacturing operations or facilities. For example, contract manufacturing organizations often need to flexibly accommodate large-, mid- and small-volume drugs, preferably within the same manufacturing facilities.

SUMMARY OF THE INVENTION

The present invention provides a manufacturing facility for the production of biopharmaceuticals that offers both batch and continuous manufacturing using at least one piece of single-use disposable technology.

The present invention also provides a manufacturing facility for the production of active pharmaceutical ingredients ("APIs") that offers both batch and continuous manufacturing using at least one piece of single-use disposable technology.

In one aspect of the invention, the manufacturing facility may include at least one piece of single-use equipment or device configured to support continuous production of biopharmaceuticals.

In another aspect of the invention, the manufacturing facility may include at least one piece of single-use equipment or device configured to support continuous production of APIs.

In another aspect of the invention, the manufacturing facility may include at least one piece of single-use equipment or device configured to support continuous production cell therapy.

In another aspect of the invention, the manufacturing facility may include at least one piece of single-use equipment or device configured to support continuous production of bulk recombinant proteins and/or monoclonal antibody products.

Furthermore, for these contract manufacturing organizations, there are a number of factors that justify the implementation of single-use technologies. For instance, there would be greater flexibility in vessel architecture and components used when designing processes to manufacture proteins and cells, significantly reduced operating costs (e.g., labor, utility, and maintenance), improved facility throughput as batch turnaround times are condensed, clean in place and steam in place operations.

Other objects, advantages and novel features of the present invention will become apparent from the following detailed description of one or more preferred embodiments when considered in conjunction with the accompanying drawings. The disclosure is written for those skilled in the art. Although the disclosure uses terminology and acronyms that may not be familiar to the layperson, those skilled in the art will be familiar with the terminology and acronyms used herein.

BRIEF DESCRIPTION OF THE DRAWINGS

In FIG. 1, "o" represents a connector and "-" represents a tube.

In FIG. 2, "o" represents a connector and "-" represents a tube.

In FIG. 3, "o" represents a connector and "-" represents a tube.

FIG. 4 insert: Top 3 cell lines selected and evaluated from a single cell line construction.

Figure 6:
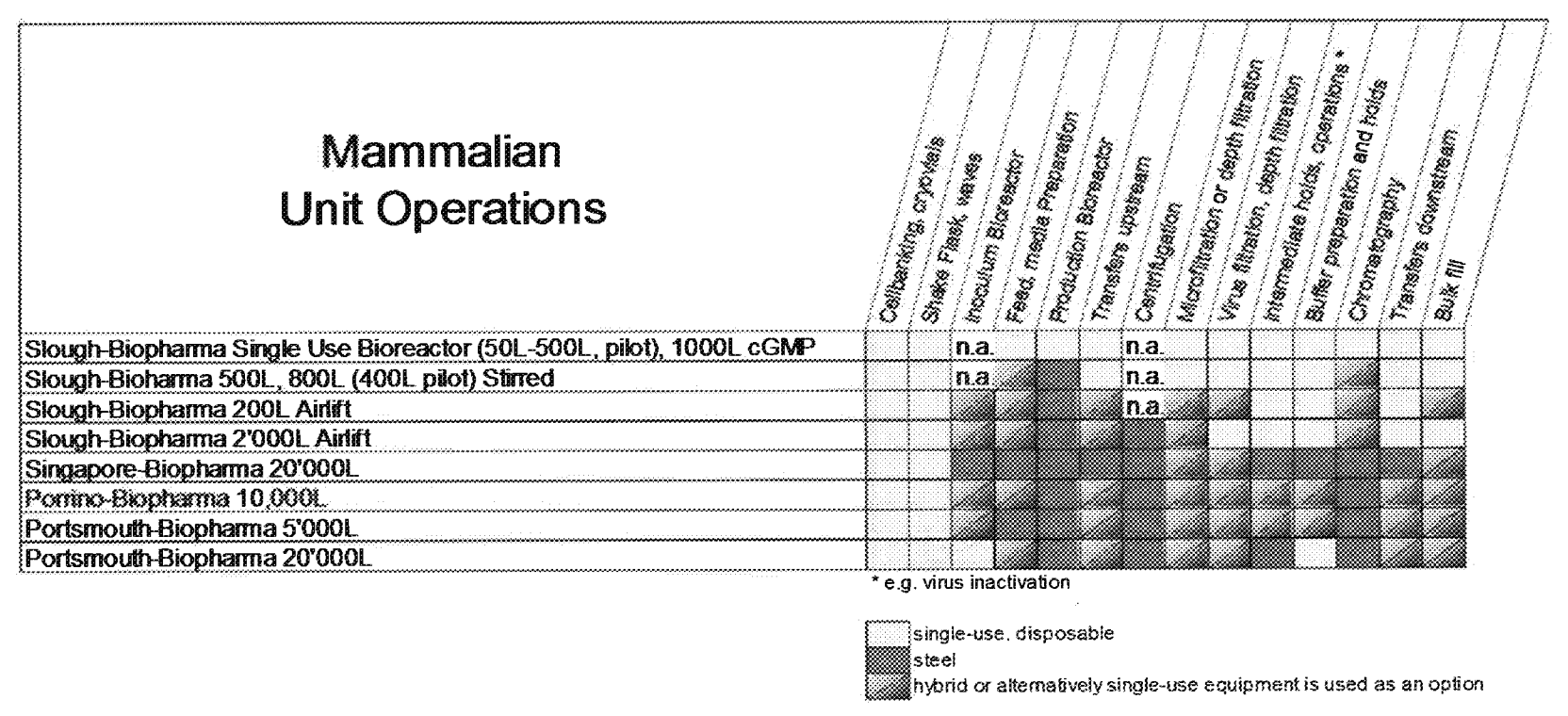

FIG. 6 shows the implementation of single-use equipment in mammalian cell-culture manufacturing facilities in accordance with one or more aspects of the invention.

DETAILED DESCRIPTION

Figure 1:
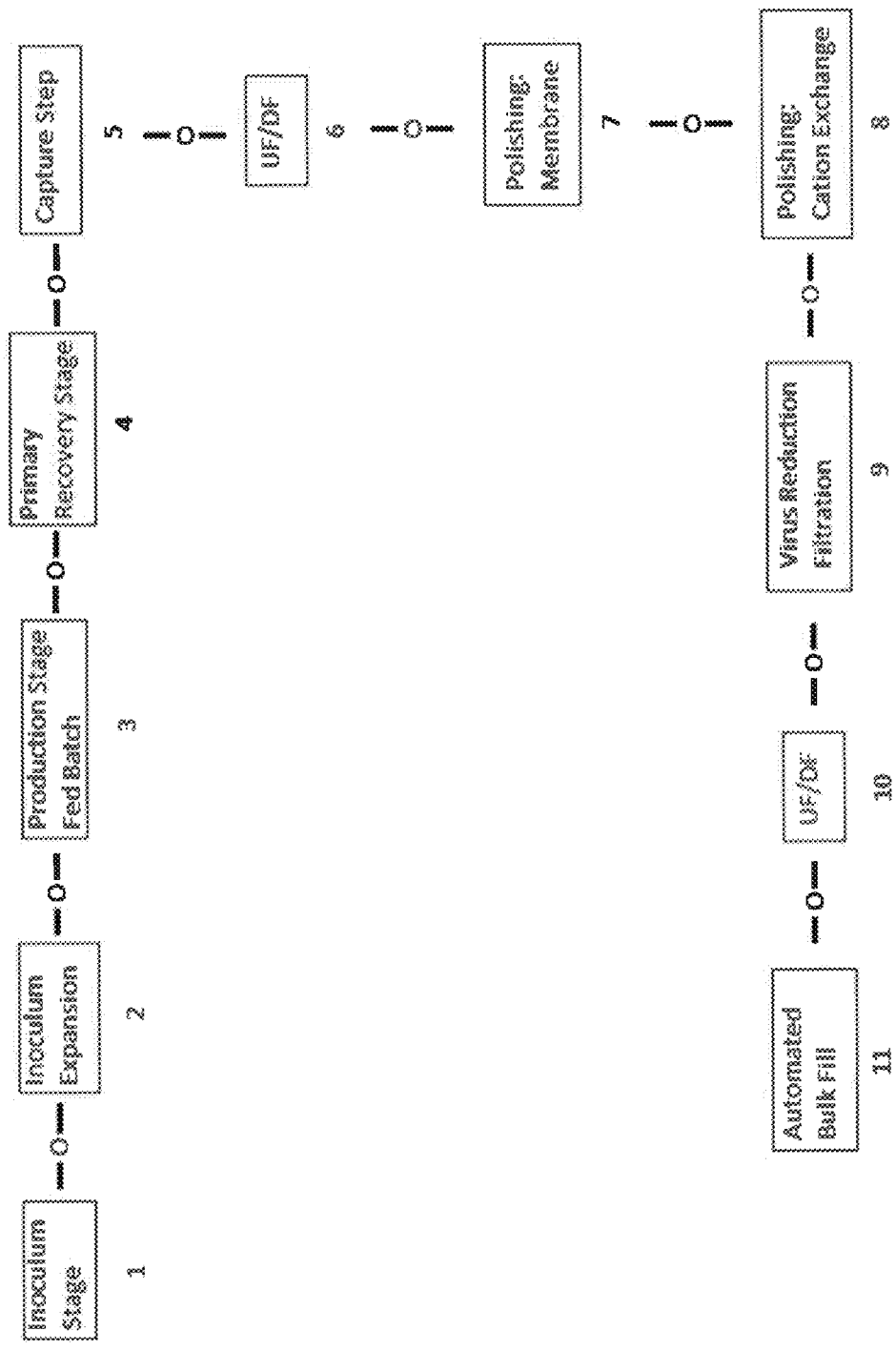
FIG. 1 is a schematic representation of batch process options with example technologies.

The present invention takes advantage of new and converging single-use technologies and integrates those technologies into a batch-fed, continuous, and/or hybrid manufacturing facilities and processes. The present invention provides improved methods, associated apparatus, and systems for manufacturing biopharmaceuticals. Provided herein are systems, facilities, means, and processes to address batch-fed, continuous, and hybrid manufacturing in a reasonable time with high yield and product quality. Also provided herein are systems, facilities, means, and processes to optimize production while reducing the risk of contamination. The disclosed methods and systems provide optimized configurations, partly or completely closed, fully disposable, and scalable production systems having integrated disposables designed for each aspect of cell production, including: input cells (1), inoculum expansion equipment (2), production stage bioreactor equipment (3), primary recovery stage equipment (4), equipment for the capture step (5), ultrafiltration and diafiltration equipment (6), polishing membranes (7), equipment for polishing using cation exchange (8), virus reduction filtration equipment (9), ultrafiltration and diafiltration equipment (10), and automated bulk fill equipment (11). The disclosed methods and systems also provide optimized configurations, partly or completely closed, fully disposable, and scalable production systems having integrated disposables designed for each aspect of cell production, including: input cells (1), inoculum expansion equipment (2), production stage perfusion equipment (12), equipment for volume exchange (13), continuous purification equipment (14), virus reduction filtration equipment (9), ultrafiltration and diafiltration equipment (10), and automated bulk fill equipment (11). In addition, the disclosed methods and systems also provide optimized configurations, partly or completely closed, fully disposable, and scalable production systems having integrated disposables designed for each aspect of cell production, including: input cells (1), inoculum expansion equipment (2), production stage bioreactor equipment (3), primary recovery stage equipment (4), equipment for volume exchange (13), continuous purification equipment (14), virus reduction filtration equipment (9), ultrafiltration and diafiltration equipment (10), and automated bulk fill equipment (11).

The present invention provides embodiments that involve a direct connection between input cells (1) and inoculum expansion equipment (2). This direct connection may also have a sensor that would allow the manufacturing process to be continuous only regarding this transfer. This would eliminate the need for a processing step involving shake flask incubation.

Moreover, the present invention provides for sensors to monitor any process variable, including, but not limited to, protein concentration, pH, conductivity, viable cell concentration, capacitance, key metabolites, temperature, titer, metabolites, glucose reuptake, DO, $CO_2$ generation, $O_2$ reuptake rate, HPLC, organic acids, saccharides, TCA intermediates, vitamins, nucleotides, elements, endotoxins, bioburdens, etc. These sensors optionally can be in communication with other sensors, and can also optionally adjust the flow rate of fluid into and/or out of at least one piece of equipment. These sensors can also be in-line sensors or at-line sensors. These sensors or their equivalents are able to communicate with the equipment, each other, a computer, the internet, or the like. Communication between sensors can be done in many ways. As just one illustrative example, communication can be accomplished using the invention as described in U.S. patent application Ser. No. 15/294,152, filed on Oct. 14, 2016. These sensors have the advantage of reducing human error in manufacturing.

Also, the present invention can be automated. For example, sensors could be used to determine seed transfer, harvest initiation, timing for process shifts, feed control, feed timing, feed flow rates, inline buffer dilution, chromatography peak cutting, VI titration, UF/DF completion, release tanks/skids, real time modification of chromatography recipes, and the like.

The present invention also provides for different pieces of manufacturing equipment, including hoses and/or connectors, to be surrounded by disposable bags such that the bags may be used to dispose of any one or more pieces of single-use items. The present invention additionally provides that one or more pieces of equipment can be in separate rooms and be connected to equipment in other rooms. Additionally, pieces that are in separate rooms may not be directly connected to those in another room but still be used as part of the present invention. Furthermore, not all of the equipment needs to be single-use equipment.

The present invention provides a methodology for selecting the optimal equipment for use in this invention. For example, factors to consider when selecting the equipment for process recovery includes: pressure, flux, pH, turbidity, acidification, capacity, cost, minimum filter area, filtration rate, de-sludge interval, efficiency, percentage of solids, storage, etc. The present invention also provides criteria for selecting bioreactors, including: mass transfer of $O_2$, cell growth, culture viability, lactate concentration, ammonium concentration, sodium concentration, potassium concentration, partial pressure of $CO_2$, glutamine concentration, osmolality, antibody concentration, temperature, oligosaccharides, the presence or absence of baffles, etc. Likewise, the present invention provides criteria for selecting equipment for continuous chromatography, such as multi-column systems, including: the interconnection of columns for an optimal use of the resin, ability to be automated or semi-automated, number of columns the can be used, amount of raw material, manufacturing time, product quality, time to process, ability to reach steady state, number of inlets, buffer consumption, higher yields at purification steps, ability to operate in batch and continuous modes depending on need, etc.

Figure 5:
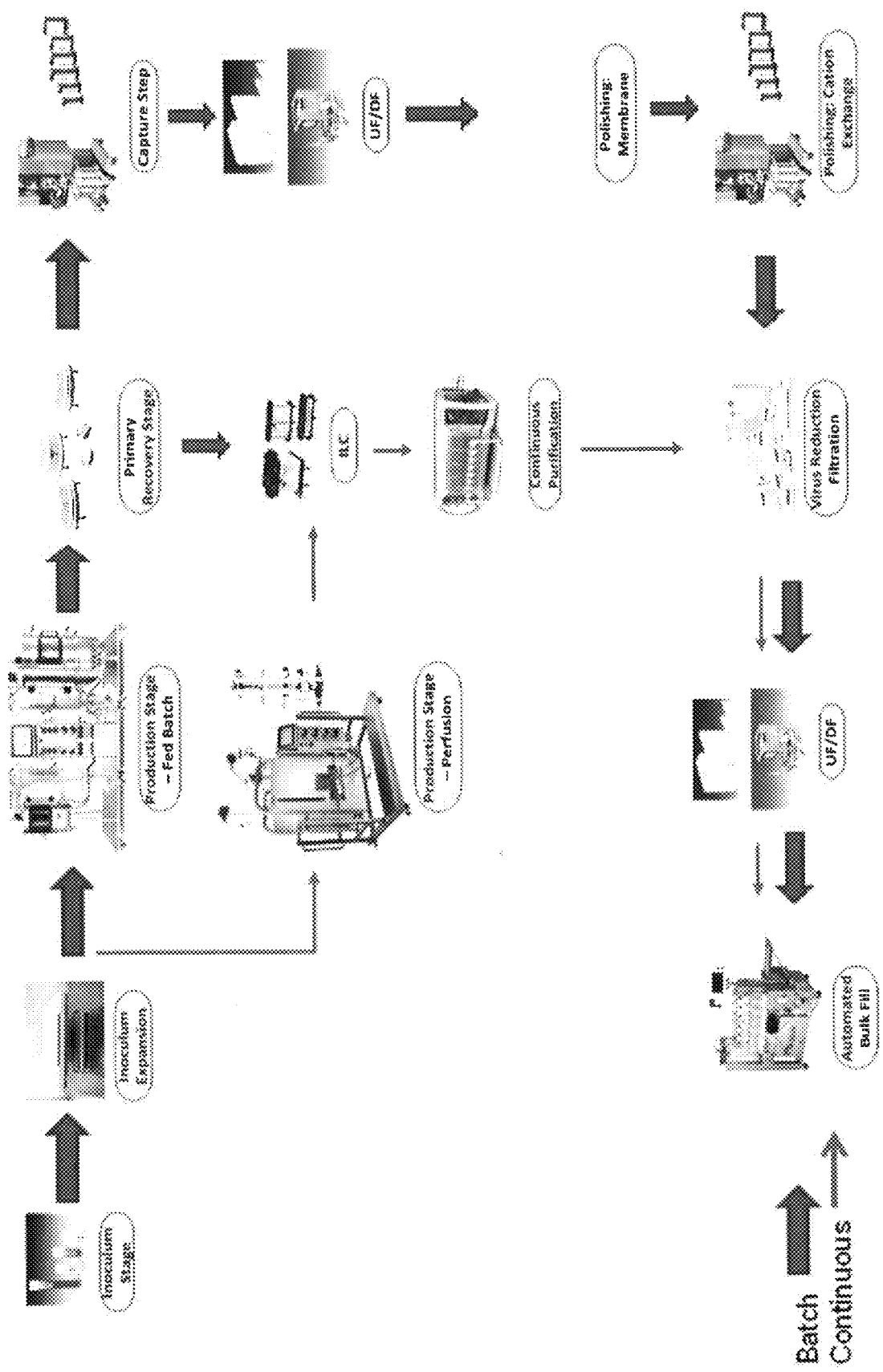
FIG. 5 is a schematic representation of continuous, batch and hybrid process options with example technologies.

FIG. 5 discloses exemplary equipment that could be used to make and use the inventions described herein. For example, the equipment for input cells (1) can be any suitable cell culture equipment including a cell culture flask, such as those commercially available from Corning Inc., that for inoculum expansion equipment (2) can be any suitable expansion equipment such as an S20 WAVE unit commercially available from General Electric Company, the production stage bioreactor equipment (3) could be any suitable bioreactor such as a BIOSTAT® system commercially available from Sartorious AG, the primary recovery stage equipment (4) could be any suitable filter recovery system such as a Zeta Plus™ recovery system commercially available from 3M, the equipment for the capture step (5) could be any suitable chromatography column such as an RTP column commercially available from General Electric Company, the ultrafiltration and diafiltration equipment (6) and (10) could be any suitable ultrafiltration and diafiltration unit such as the Hydrosart® commercially available from Sartorious AG, the polishing membranes (7) could be any suitable membranes such as those that are commercially available from Sartorius AG, the equipment for polishing using cation exchange (8) could be any suitable chromatography column such as an RTP column commercially available from General Electric Company, the virus reduction filtration equipment (9) could be any suitable virus reduction system such as the Planova™ 20N commercially available from Asahi Kasei Medical Co., Ltd., the automated bulk fill equipment (11) could be any suitable fill equipment sucg as the SciLog® SciFlex® Filter and Dispense System commercially available from Parker Domnick Hunter, the production stage perfusion equipment (12) could be any suitable production stage perfusion reactor equipment such as the Allegro STR bioreactor family commercially available from Pall Corporation and/or the XCell™ ATF system commercially available from Repligen Corporation, the equipment for volume exchange (13) could be any suitable volume exchange equipment such as the ILC system commercially available from Pall Corporation, and the continuous purification equipment (14) could be any suitable purification equipment such as the BioSMB system commercially available from Pall Corporation.

In addition, it is an object of the present invention that these Batch-fed, continuous, and/or hybrid manufacturing facilities and processes can be done in one or more facilities. For example, one or more steps could be done in one or more separate facilities from the others. It is an object of the present invention that these processes can comply with state, federal, and international regulations regarding Good Manufacturing Processes.

Batch-fed, continuous, and/or hybrid manufacturing facilities and processes each have their advantages and disadvantages that depend on numerous factors such as, but not limited to, cost, cell-type, output volume requirements, and the like. Therefore, it is an object of the present invention to be able to switch between any of these processes and facilities. Such modifications could be quick, timely and/or inexpensive. Such modifications could be done in such a way as to minimize the risk of contamination by, for example, inadvertent dripping on the manufacturing floor from any of the tubes, connectors, machines, or the like. For example, at least one tube between manufacturing components could include a single use tube. Likewise, at least one connector that connects a tube to a piece of manufacturing equipment could be a single use connector. As well, more than one of these connecting tubes and/or connectors could be a single-use item.

It is another object of the present invention to use at least one piece of single-use manufacturing equipment in the manufacturing facilities and processes of the present invention.

It is another object of the present invention to use at least one piece of single-use connection equipment in the manufacturing facilities and processes of the present invention.

Figure 2:
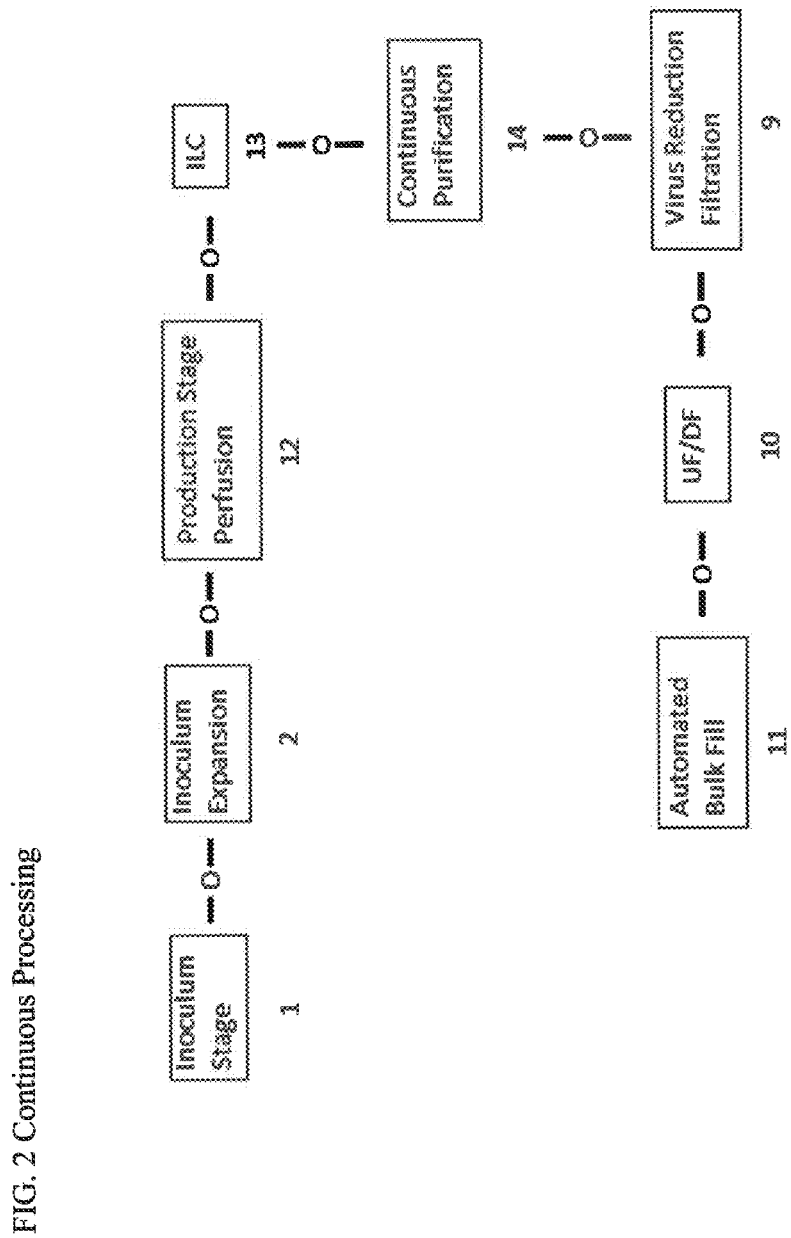
FIG. 2 is a schematic representation of continuous process options with example technologies.
Figure 3:
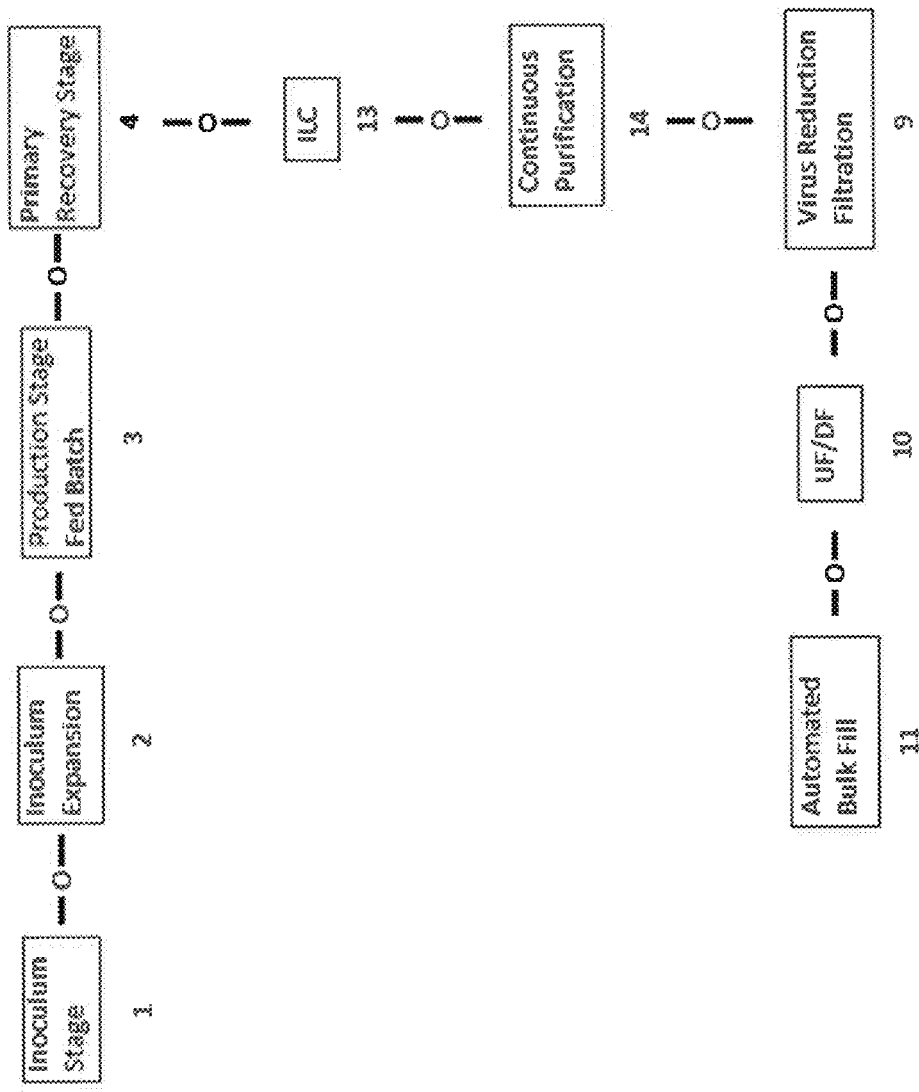
FIG. 3 is a schematic representation of hybrid process options with example technologies.

The goal is to move towards a continuous process option in which the product moves directly from one step to the next without any significant intervening product hold (see e.g., FIGS. 1, 2, and 3).

Preferably, the continuous process would operate at a true steady-state, with the operating conditions (e.g., flow rates and pressures) and product/impurity concentrations remaining constant throughout the process. With this, fully integrated, continuous single-use bioprocessing would allow for predictable steady manufacture at smaller scales (therefore requiring smaller equipment and reducing footprint in existing plants and minimizes the size of new plants) with the associated cost savings and benefits. This fully integrated system could also be operated on a larger scale, if such were needed.

The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products-such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesized by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, single-use and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797, 2012/0077429, 2011/0280797, 2009/0305626, and U.S. Pat. Nos. 8,298,054, 7,629,167, and 5,656,491, each of which are hereby incorporated by reference in its entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g., mouse myeloma (NSO)-cell lines, Chinese hamster ovary (CHO)-cell lines, HTI080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g., a yeast cell (e.g., *Pichia* genus (e.g., *Pichia pastoris, Pichia methanolica, Pichia kluyveri*, and *Pichia angusta*), *Komagataella* genus (e.g., *Komagataella pastoris, Komagataella pseudopastoris* or *Komagataella phaffii*), *Saccharomyces* genus (e.g., *Saccharomyces cerevisae, cerevisiae, Saccharomyces kluyveri, Saccharomyces uvarum*), *Kluyveromyces* genus (e.g., *Kluyveromyces lactis, Kluyveromyces marxianus*), the *Candida* genus (e.g., *Candida utilis, Candida cacaoi, Candida boidinii*), the *Geotrichum* genus (e.g., *Geotrichum fermentans*), *Hansenula polymorpha, Yarrowia lipolytica*, or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g., *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina,* or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus. Bacillus* that can be used is, e.g. the *B. subtilis, B. amyloliquefaciens, B. lichentformis, B. natto,* or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus Ohio 43210-1214.

In one embodiment, the prokaryotic cell is a Gram-negative cell, such as *Salmonella* spp. or *Escherichia coli,* such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-la), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostirn, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant CI esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, lSAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AID-SVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-I, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor VIII (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OSI, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of U.S. Patent Publication No. 2016/0097074:

TABLE I

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |

TABLE I-continued

| Protein Product | Reference Listed Drug |
|---|---|
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |

TABLE I-continued

| Protein Product | Reference Listed Drug |
|---|---|
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molecule, fusion protein, protein vaccine, or peptide as shown in Table 2.

TABLE 2

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel |
| | Lutropin-α | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |
| Blood Clotting/Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/Growth factor | Type I alpha-interferon | Infergen |
| | Interferon-αn3 (IFNαn3) | Alferon N |
| | Interferon-β1a (rIFN-β) | Avonex, Rebif |
| | Interferon-β1b (rIFN-β) | Betaseron |
| | Interferon-γ1b (IFNγ) | Actimmune |
| | Aldesleukin (interleukin 2(IL2), epidermal theymocyte activating factor; ETAF Palifermin (keratinocyte growth factor; KGF) | Proleukin Kepivance Regranex Anril, Kineret |
| | Becaplemin (platelet-derived growth factor; PDGF) | |
| | Anakinra (recombinant IL1 antagonist) | |
| Antibody molecules | Bevacizumab (VEGFA mAb) | Avastin |
| | | Erbitux |
| | Cetuximab (EGFR mAb) | Vectibix |
| | Panitumumab (EGFR mAb) | Campath |

TABLE 2-continued

Exemplary Products

| Therapeutic Product type | Product | Trade Name |
|---|---|---|
| | Alemtuzumab (CD52 mAb) | Rituxan |
| | Rituximab (CD20 chimeric Ab) | Herceptin |
| | Trastuzumab (HER2/Neu mAb) | Orencia |
| | Abatacept (CTLA Ab/Fc fusion) | Humira |
| | Adalimumab (TNFαmAb) | Enbrel |
| | Etanercept (TNF receptor/Fc fusion) | Remicade |
| | Infliximab (TNFαchimeric mAb) | Amevive |
| | Alefacept (CD2 fusion protein) | Raptiva |
| | Efalizumab (CD11a mAb) | Tysabri |
| | Natalizumab (integrin α4 subunit mAb) | Soliris |
| | Eculizumab (C5mAb) | Orthoclone, OKT3 |
| | Muromonab-CD3 | |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

In particular, for protein manufacturing, technical, quality and economical aspects may be considered when implementing single-use technologies into a mammalian manufacturing facility. Most of the mammalian manufacturing facilities are designed for the manufacture of multiple products. Consequently these facilities allow, to a certain extent, for flexibility regarding type of product, volume requirements and sequence/type of unit operations. The facility and room design of the various manufacturing facilities can be also taken into consideration when implementing single-use technology at the time of construction to ensure that these facilities allow for potential future use of one or more pieces of single-use equipment.

For cell therapy manufacturing, the facilities may be designed with a focus on flexibility and are able to handle products at various stages in the clinical pipeline. For processes previously developed in 2D culture systems and at early clinical stages, the main single-use component for the upstream expansion would be multilayer vessels (cell factories). Currently, the manufacturing facilities are able to handle various types and batch sizes of these vessels. However, as these processes get closer to commercialization and the need for larger yields-per-lot grows the switch to single-use bioreactor and microcarrier based processes may be necessary. Thus, it may be preferable to develop a single-use 3D bioreactor platform capable of supporting production scales from 1 L to 50 L. More preferably, to expand the production scale to 200 L. Preferably, for cell therapy manufacturing, the implementation of single-use technology is carried out as early as possible to ensure that the product is commercialization-ready from the very beginning and that comparability issues are averted late in the development cycle.

The present invention relates to a manufacturing facility for the production of biopharmaceuticals and or APIs that offers both batch and continuous manufacturing using single-use disposable technology. As one example, the manufacturing facility according to the present invention is a biopharmaceutical facility with the capacity capable of manufacturing bulk recombinant proteins and/or monoclonal antibody products. As another example, the manufacturing facility according to the present invention is a biopharmaceutical facility with the capacity capable of manufacturing cell therapy. As an additional example, the manufacturing facility according to the present invention is a biopharmaceutical facility with the capacity capable of manufacturing APIs.

Figure 4:
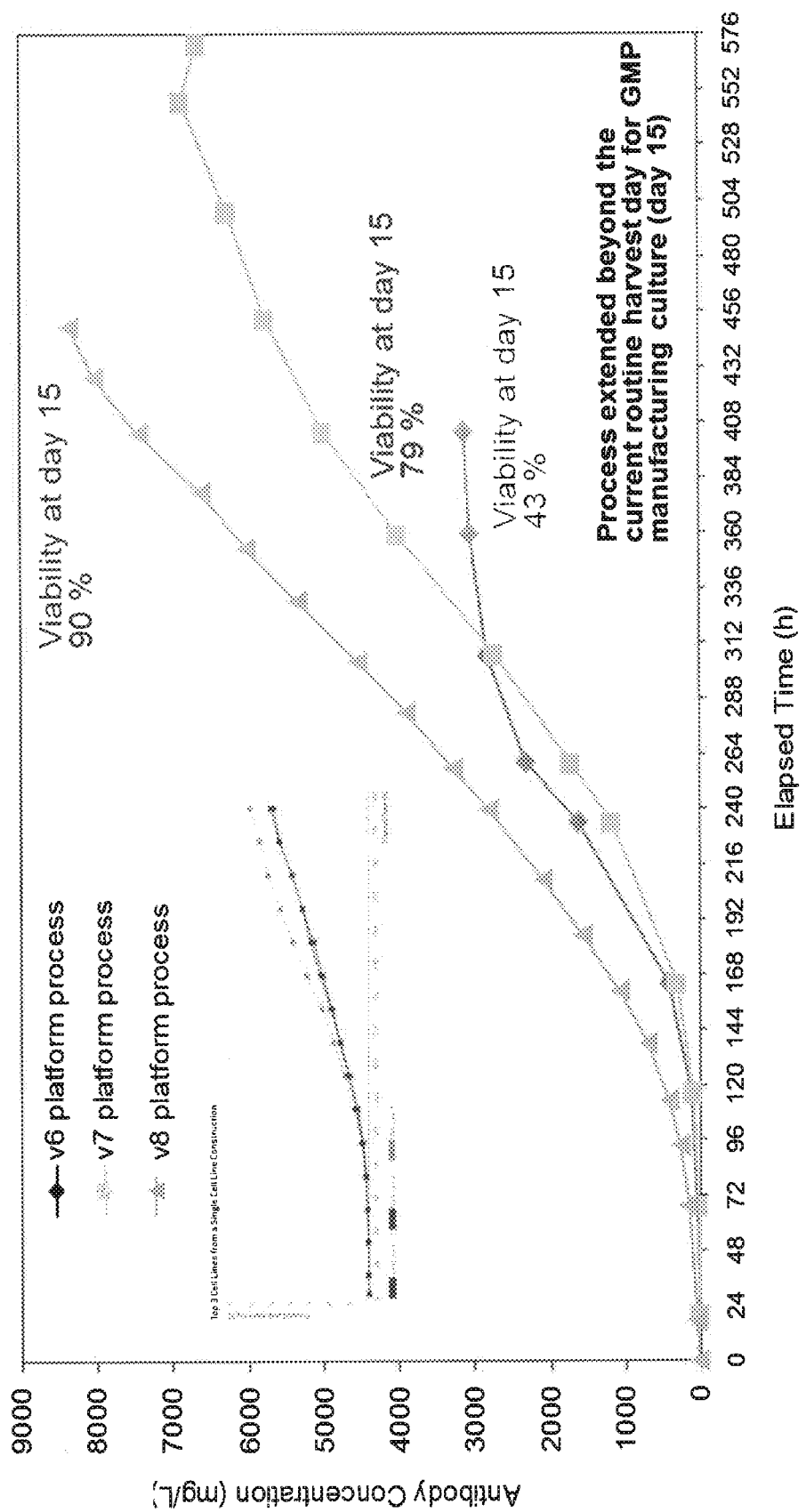
FIG. 4 shows antibody concentration profiles for a Model GS-CHO Cell Line in laboratory-scale bioreactors with a comparison between the Version 6, Version 7 and Version 8 platform processes.

In one aspect of the invention, the manufacturing facility may include single-use equipment or devices configured to support continuous production of biopharmaceuticals. The biopharmaceutical products include, but are not limited to, recombinant proteins, monoclonal antibodies, protein-drug conjugates, viral based therapeutics and cell therapies. Preferably, the single-use equipment or devices would dominate small- and mid-scale bioprocessing and occupy larger scale manufacturing. As one example, as shown in FIG. 2, the implementation of various single-use equipment in connection with small-, mid- and large-scale bioreactors. In another example, studies have shown that antibody production through the use of Glutamine Synthetase-Chinese Hamster Ovary (GS-CHO) cell lines increases with robust manufacturing process which can be achieved using one of the continuous single-use disposable manufacturing facility of the present invention (see e.g., FIG. 4).

In one aspect of the invention, a method to manufacture a biopharmaceutical product is provided including: inserting a material into an inoculum device for processing; transferring the material from the inoculum device to an inoculum expansion device for further processing; then transferring the material from the inoculum expansion device to a production stage bioreactor device for further processing; then transferring the material from the production stage bioreactor device to a primary recovery device for further processing; then transferring the material from the primary recovery device to a capturing device for further processing; then transferring the material from the capturing device to an ultrafiltration and diafiltration device for further processing; then transferring the material from the ultrafiltration and diafiltration device to a polishing membrane device for further processing; then transferring the material from the polishing membrane device to a polishing using cation exchange device for further processing; then transferring the material from the polishing using cation exchange device to a virus reduction filtration device for further processing; then transferring the material from the virus reduction filtration device to an ultrafiltration and diafiltration device for further processing; and then transferring the material from the ultrafiltration and diafiltration device to an automated bulk fill device to obtain the biopharmaceutical product.

In another aspect of the invention, a method to manufacture a biopharmaceutical product is provided including: inserting a material into an inoculum device for processing; transferring the material from the inoculum device to an inoculum expansion device for further processing; then transferring the material from the inoculum expansion device to a production stage perfusion device for further processing; then transferring the material from the production stage perfusion device to a volume exchange device for further processing; then transferring the material from the volume exchange device to a continuous filtration device for further processing; then transferring the material from the continuous filtration device to a virus reduction filtration device for further processing; then transferring the material from the virus reduction filtration device to an ultrafiltration and diafiltration device for further processing; and then transferring the material from the ultrafiltration and diafiltration device to an automated bulk fill device to obtain the biopharmaceutical product.

In another aspect of the invention, a method to manufacture a biopharmaceutical product is provided including: inserting a material into an inoculum device for processing; transferring the material from the inoculum device to an inoculum expansion device for further processing; then transferring the material from the inoculum expansion device to a production stage bioreactor device for further processing; then transferring the material from the production stage bioreactor device to a primary recovery device for further processing; then transferring the material from the primary recovery device to a volume exchange device for further processing; then transferring the material from the volume exchange device to a continuous purification device for further processing; then transferring the material from the continuous purification device to a virus reduction filtration device for further processing; then transferring the material from the virus reduction filtration device to an ultrafiltration and diafiltration device for further processing; and then transferring the material from the ultrafiltration and diafiltration device to an automated bulk fill device to obtain the biopharmaceutical product.

In another aspect of the invention, a method to manufacture a biopharmaceutical product is provided including: inserting a material into an inoculum device for processing; transferring the material from the inoculum device to an inoculum expansion device for further processing; then transferring the material from the inoculum expansion device to a production stage perfusion device for further processing; then transferring the material from the production stage perfusion device to a volume exchange device for further processing; then transferring the material from the volume exchange device to a continuous purification device for further processing; then transferring the material from the continuous purification device to a virus reduction filtration device for further processing; then transferring the material from the virus reduction filtration device to an ultrafiltration and diafiltration device for further processing; and then transferring the material from the ultrafiltration and diafiltration device to an automated bulk fill device to obtain the biopharmaceutical product.

In another aspect of the invention, a manufacturing system for biopharmaceuticals is provided comprising: at least one inputting device connected to at least one inoculum expansion device through at least one piece of tubing and a connector; said at least one inoculum expansion device is connected to at least one production stage bioreactor device through at least one piece of tubing and a connector; said at least one production stage bioreactor device is connected to at least one primary recovery device through at least one piece of tubing and a connector; said at least one primary recovery device is connected to at least one capturing device through at least one piece of tubing and a connector; said at least one capturing device is connected to at least one ultrafiltration and diafiltration device through at least one piece of tubing and a connector; said at least one ultrafiltration and diafiltration device is connected to at least one polishing membranes device through at least one piece of tubing and a connector; said at least one polishing membranes device is connected to at least one polishing using cation exchange device through at least one piece of tubing and a connector; said at least one polishing using cation exchange device is connected to at least one virus reduction filtration device through at least one piece of tubing and a connector; and said at least one virus reduction filtration device is connected to at least one ultrafiltration and diafiltration device through at least one piece of tubing and a connector, said at least one ultrafiltration and diafiltration device is connected to at least one automated bulk fill device through at least one piece of tubing and a connector.

In another aspect of the invention, a manufacturing system for biopharmaceuticals is provided comprising: A method of making biopharmaceuticals comprising: connecting at least one inputting device to at least one inoculum expansion device using at least one piece of tubing and a connector such that material can pass from the inputting device to the inoculum expansion device; connecting said at least one inoculum expansion device to at least one production stage bioreactor device using at least one piece of tubing and a connector such that material can pass from the inoculum expansion device to the production stage bioreactor device; connecting said at least one production stage bioreactor device to at least one primary recovery device using at least one piece of tubing and a connector such that material can pass from the production stage bioreactor device to the primary recovery device; connecting said at least one primary recovery device to at least one capturing device using at least one piece of tubing and a connector such that material can pass from the primary recovery device to the capturing device; connecting said at least one capturing device to at least one ultrafiltration and diafiltration device using at least one piece of tubing and a connector such that material can pass from the capturing device to the ultrafiltration and diafiltration device; connecting said at least one ultrafiltration and diafiltration device to at least one polishing membranes device using at least one piece of tubing and a connector such that material can pass from the ultrafiltration and diafiltration device to the polishing membrane device; connecting said at least one polishing membranes device to at least one polishing using cation exchange device using at least one piece of tubing and a connector such that material can pass from the polishing membranes device to the polishing using cation exchange device; and connecting said at least one polishing using cation exchange device to at least one virus reduction filtration device using at least one piece of tubing and a connector such that material can pass from the polishing using cation exchange device to the virus reduction filtration device; connecting said at least one virus reduction filtration device to at least one ultrafiltration and diafiltration device such that material can pass from the virus reduction filtration device to the ultrafiltration and diafiltration device; and connecting said at least one ultrafiltration and diafiltration device to at least one automated bulk fill device such that material can pass from the ultrafiltration and diafiltration device to the automated bulk fill device.

In another aspect of the invention, a manufacturing system for biopharmaceuticals is provided comprising: at least one inputting device connected to at least one inoculum expansion device through at least one piece of tubing and a connector; said at least one inoculum expansion device is connected to at least one production stage perfusion device through at least one piece of tubing and a connector, said at least one production stage perfusion device is connected to at least one volume exchange device through at least one piece of tubing and a connector, said at least one volume exchange device is connected to at least one continuous filtration device through at least one piece of tubing and a connector; said at least one continuous filtration device is connected to at least one virus reduction filtration device through at least one piece of tubing and a connector; said at least one virus reduction filtration device is connected to at least one ultrafiltration and diafiltration device through at least one piece of tubing and a connector; and said at least one ultrafiltration and diafiltration device is connected to at least one automated bulk fill device through at least one piece of tubing and a connector.

In another aspect of the invention, a method of making biopharmaceuticals is provided comprising: connecting at least one inputting device to at least one inoculum expansion device using at least one piece of tubing and a connector such that material can pass from the inputting device to the inoculum expansion device; connecting said at least one inoculum expansion device to at least one production stage perfusion device using at least one piece of tubing and a connector such that material can pass from the inoculum expansion device to the production stage perfusion device; connecting said at least one production stage perfusion device to at least one volume exchange device using at least one piece of tubing and a connector such that material can pass from the production stage perfusion device to the volume exchange device; connecting said at least one volume exchange device to at least one continuous purification device using at least one piece of tubing and a connector such that material can pass from the volume exchange device to the continuous purification device; connecting said at least one continuous purification device to at least one virus reduction filtration device using at least one piece of tubing and a connector such that material can pass from the continuous purification device to the virus reduction filtration device; connecting said at least one virus reduction filtration device to at least one ultrafiltration and diafiltration device using at least one piece of tubing and a connector such that material can pass from the virus reduction filtration device to the ultrafiltration and diafiltration device; and connecting said at least one ultrafiltration and diafiltration device to at least one automated bulk fill device using at least one piece of tubing and a connector such that material can pass from the ultrafiltration and diafiltration device to the automated bulk fill device.

In another aspect of the invention, a manufacturing system for biopharmaceuticals is provided comprising: at least one inputting device connected to at least one inoculum expansion device through at least one piece of tubing and a connector; said at least one inoculum expansion device is connected to at least one production stage bioreactor device through at least one piece of tubing and a connector; said at least one production stage bioreactor device is connected to at least one primary recovery device through at least one piece of tubing and a connector; said at least one primary recovery device is connected to at least one volume exchange device through at least one piece of tubing and a connector; said at least one volume exchange device is connected to at least one continuous purification device through at least one piece of tubing and a connector, said at least one continuous purification device is connected to at least one virus reduction filtration device through at least one piece of tubing and a connector, said at least one virus reduction filtration device is connected to at least one ultrafiltration and diafiltration device through at least one piece of tubing and a connector; and said at least one ultrafiltration and diafiltration device is connected to at least one automated bulk fill device through at least one piece of tubing and a connector.

In another aspect of the invention, a method of making biopharmaceuticals is provided comprising: connecting at least one inputting device to at least one inoculum expansion device using at least one piece of tubing and a connector such that material can pass from the inputting device to the inoculum expansion device; connecting said at least one inoculum expansion device to at least one production stage bioreactor device using at least one piece of tubing and a connector such that material can pass from the inoculum expansion device to the production stage bioreactor device; connecting said at least one production stage bioreactor device to at least one primary recovery device using at least one piece of tubing and a connector such that material can pass from the production stage bioreactor device to the primary recovery device; connecting said at least one primary recovery device to at least one volume exchange device using at least one piece of tubing and a connector such that material can pass from the primary recovery device to the volume exchange device; connecting said at least one volume exchange device to at least one continuous purification device using at least one piece of tubing and a connector such that material can pass from the volume exchange device to the continuous purification device; connecting said at least one continuous purification device to at least one virus reduction filtration device using at least one piece of tubing and a connector such that material can pass from the continuous purification device to the virus reduction filtration device; connecting said at least one virus reduction filtration device to at least one ultrafiltration and diafiltration device using at least one piece of tubing and a connector such that material can pass from the virus reduction filtration device to the ultrafiltration and diafiltration device; and connecting said at least one ultrafiltration and diafiltration device to at least one automated bulk fill device using at least one piece of tubing and a connector such that material can pass from the ultrafiltration and diafiltration device to the automated bulk fill device.

In another aspect of the invention, a manufacturing system for biopharmaceuticals is provided comprising: at least one inputting device connected to at least one inoculum expansion device through at least one piece of tubing and a connector; said at least one inoculum expansion device is connected to at least one production stage perfusion device through at least one piece of tubing and a connector; said at least one production stage perfusion device is connected to at least one volume exchange device through at least one piece of tubing and a connector, said at least one volume exchange device is connected to at least one continuous purification device through at least one piece of tubing and a connector; said at least one continuous purification device is connected to at least one virus reduction filtration device through at least one piece of tubing and a connector, said at least one virus reduction filtration device is connected to at least one ultrafiltration and diafiltration device through at least one piece of tubing and a connector; and said at least one ultrafiltration and diafiltration device is connected to at least one automated bulk fill device through at least one piece of tubing and a connector.

In another aspect of the invention, a method for manufacturing biopharmaceuticals is provided comprising: connecting at least one inputting device to at least one inoculum expansion device using at least one piece of tubing and a connector such that material can pass from the inputting device to the inoculum expansion device; connecting said at least one inoculum expansion device to at least one production stage bioreactor device using at least one piece of tubing and a connector such that material can pass from the inoculum expansion device to the production stage bioreactor device; connecting said at least one production stage bioreactor device to at least one primary recovery device using at least one piece of tubing and a connector such that material can pass from the production stage bioreactor device to the primary recovery device; connecting said at least one primary recovery device to at least one volume exchange device using at least one piece of tubing and a connector such that material can pass from the primary recovery device to the volume exchange device; connecting said at least one volume exchange device to at least one continuous purification device using at least one piece of tubing and a connector such that material can pass from the volume exchange device to the continuous purification device; connecting said at least one continuous purification device to at least one virus reduction filtration device using at least one piece of tubing and a connector such that material can pass from the continuous purification device to the virus reduction filtration device; connecting said at least one virus reduction filtration device to at least one ultrafiltration and diafiltration device using at least one piece of tubing and a connector such that material can pass from the virus reduction filtration device to the ultrafiltration and diafiltration device; and connecting said at least one ultrafiltration and diafiltration device to at least one automated bulk fill device using at least one piece of tubing and a connector such that material can pass from the ultrafiltration and diafiltration device to the automated bulk fill device.

In another aspect of the invention, a manufacturing system for biopharmaceuticals is provided comprising: at least one equipment configured for inputting cells; at least one equipment configured for inoculum expansion; at least one production stage bioreactor; at least one equipment configured for primary recovery, at least one equipment configured for capturing; at least one equipment configured for ultrafiltration and diafiltration; at least one equipment configured for polishing membranes; at least one equipment configured for polishing using cation exchange; at least one equipment configured for virus reduction filtration; and at least one equipment configured for automated bulk fill; and wherein the equipments are connected, and wherein the at least one equipment is connected through at least one piece of tubing and at least one connector such that the contents can pass from one piece of equipment to another via tubing.

In another aspect of the invention, a method for manufacturing biopharmaceuticals is provided comprising: providing at least one equipment configured for inputting cells; providing at least one equipment configured for inoculum expansion; providing at least one production stage bioreactor; providing at least one equipment configured for primary recovery, providing at least one equipment configured for capturing; providing at least one equipment configured for ultrafiltration and diafiltration; providing at least one equipment configured for polishing membranes; providing at least one equipment configured for polishing using cation exchange; providing at least one equipment configured for virus reduction filtration; providing a connector between the at least one equipment configured for inputting cells and the at least one equipment configured for inoculum expansion; providing a connector between the at least one equipment configured for inoculum expansion and the at least one production stage bioreactor, providing a connector between the least one production stage bioreactor and the at least one equipment configured for primary recovery; providing a connector between the at least one equipment configured for primary recovery and the at least one equipment configured for capturing; providing a connector between the at least one equipment configured for capturing and the at least one equipment configured for ultrafiltration and diafiltration; providing a connector between the at least one equipment configured for ultrafiltration and diafiltration and the at least one equipment configured for polishing membranes; providing a connector between the at least one equipment configured for polishing membranes and the at least one equipment configured for polishing using cation exchange; providing a connector between the at least one equipment configured for polishing using cation exchange and the at least one equipment configured for virus reduction filtration; providing at least one equipment configured for ultrafiltration and diafiltration; providing at least one equipment configured for automated bulk fill; providing a connector between the at least one equipment configured for virus reduction filtration and the at least one equipment configured for ultrafiltration and diafiltration; providing a connector between the at least one equipment configured for ultrafiltration and diafiltration and the at least one equipment configured for automated bulk fill.

In another aspect of the invention, a method for manufacturing biopharmaceuticals is provided comprising: providing at least one equipment configured for inputting cells; providing at least one equipment configured for inoculum expansion; providing a connector between the at least one equipment configured for inputting cells and the at least one equipment configured for inoculum expansion.

In another aspect of the invention, a manufacturing system for biopharmaceuticals is provided comprising: at least one equipment configured for inputting cells; at least one equipment configured for inoculum expansion; at least one equipment configured for production stage perfusion; at least one equipment configured for volume exchange; at least one equipment configured for continuous purification; at least one equipment configured for virus reduction filtration; at least one equipment configured for ultrafiltration and diafiltration; and at least one equipment configured for automated bulk fill; and wherein the equipments are connected, and wherein the at least one equipment is connected through at least one piece of tubing and at least one connector such that the contents can pass from one piece of equipment to another via tubing.

In another aspect of the invention, a method for manufacturing biopharmaceuticals is provided comprising: providing at least one equipment configured for inputting cells; providing at least one equipment configured for inoculum expansion; providing at least one equipment configured for production stage perfusion; providing at least one equipment configured for volume exchange; providing at least one equipment configured for continuous purification; providing at least one equipment configured for virus reduction filtration; providing at least one equipment configured for ultrafiltration and diafiltration; providing at least one equipment configured for automated bulk fill; providing a connector between the at least one equipment configured for inputting cells and the at least one equipment configured for inoculum expansion; providing a connector between the at least one equipment configured for inoculum expansion and at least one equipment configured for production stage perfusion; providing a connector between the at least one equipment configured for production stage perfusion and the at least one equipment configured for volume exchange; providing a connector between the at least one equipment configured for volume exchange and the at least one equipment configured for continuous purification; providing a connector between the at least one equipment configured for continuous purification and the at least one equipment configured for virus reduction filtration; providing a connector between the at least one equipment configured for virus reduction filtration and the at least one equipment configured for ultrafiltration and diafiltration; providing a connector between the at least one equipment configured for ultrafiltration and diafiltration and the at least one equipment configured for automated bulk fill.

In another aspect of the invention, a manufacturing system for biopharmaceuticals is provided comprising: at least one equipment configured for inputting cells; at least one equipment configured for inoculum expansion; at least one production stage bioreactor, at least one equipment configured for primary recovery; at least one equipment configured for volume exchange; at least one equipment configured for continuous purification; at least one equipment configured for virus reduction filtration; at least one equipment configured for ultrafiltration and diafiltration; and at least one equipment configured for automated bulk fill; and wherein the equipments are connected, and wherein the at least one equipment is connected through at least one piece of tubing and at least one connector such that the contents can pass from one piece of equipment to another via tubing.

In another aspect of the invention, a method for manufacturing biopharmaceuticals is provided comprising: providing at least one equipment configured for inputting cells; providing at least one equipment configured for inoculum expansion; providing at least one production stage bioreactor; providing at least one equipment configured for primary recovery stage; providing at least one equipment configured for volume exchange; providing at least one equipment configured for continuous purification; providing at least one equipment configured for virus reduction filtration; providing at least one equipment configured for ultrafiltration and diafiltration; providing at least one equipment configured for automated bulk fill; providing a connector between the at least one equipment configured for inputting cells and the at least one equipment configured for inoculum expansion; providing a connector between the at least one equipment configured for inoculum expansion and the at least one production stage bioreactor, providing a connector between the at least one production stage bioreactor and at least one equipment configured for primary recovery; providing a connector between the at least one equipment configured for primary recovery and the at least one equipment configured for volume exchange; providing a connector between the at least one equipment configured for volume exchange and the at least one equipment configured for continuous purification; providing a connector between the at least one equipment configured for continuous purification and the at least one equipment configured for virus reduction filtration; providing a connector between the at least one equipment configured for virus reduction filtration and the at least one equipment configured for ultrafiltration and diafiltration; providing a connector between the at least one equipment configured for ultrafiltration and diafiltration and the at least one equipment configured for automated bulk fill.

In another aspect of the invention, a manufacturing system for biopharmaceuticals is provided comprising: at least one equipment configured for inputting cells; at least one equipment configured for inoculum expansion; at least one equipment configured for production stage perfusion; at least one equipment configured for volume exchange; at least one equipment configured for continuous purification; at least one equipment configured for virus reduction filtration; at least one equipment configured for ultrafiltration and diafiltration; and at least one equipment configured for automated bulk fill; and wherein the equipments are connected, and wherein the at least one equipment is connected through at least one piece of tubing and at least one connector such that the contents can pass from one piece of equipment to another via tubing.

In another aspect of the invention, a method for manufacturing biopharmaceuticals is provided comprising: providing at least one equipment configured for inputting cells; providing at least one equipment configured for inoculum expansion; providing at least one production stage bioreactor; providing at least one equipment configured for primary recovery; providing at least one equipment configured for volume exchange; providing at least one equipment configured for continuous purification; providing at least one equipment configured for virus reduction filtration; providing at least one equipment configured for ultrafiltration and diafiltration; providing at least one equipment configured for automated bulk fill equipment; providing a connector between the at least one equipment configured for inputting cells and the at least one equipment configured for inoculum expansion; providing a connector between the at least one equipment configured for inoculum expansion and the at least one production stage bioreactor; providing a connector between the at least one production stage bioreactor and the at least one equipment configured for volume exchange; providing a connector between the at least one equipment configured for volume exchange and the at least one equipment configured for continuous purification; providing a connector between the at least one equipment configured for continuous purification and the at least one equipment configured for virus reduction filtration; providing a connector between the at least one equipment configured for virus reduction filtration and the at least one equipment configured for ultrafiltration and diafiltration; providing a connector between the at least one equipment configured for ultrafiltration and diafiltration and the at least one equipment configured for automated bulk fill.

In another aspect of the invention, a manufacturing system for biopharmaceuticals is provided comprising: at least one equipment configured for inputting cells; at least one equipment configured for inoculum expansion; and a connector between the at least one equipment configured for inputting cells and the at least one equipment configured for inoculum expansion.

In yet another aspect of the invention, the device or equipment can be from at least two different manufacturers.

In yet another aspect of the invention, at least one device is not made for single-use.

In yet another aspect of the invention, the manufacturing system is operated as a closed system.

In yet another aspect of the invention, the manufacturing system further includes at least one sensor capable of controlling flow of material between two devices.

In yet another aspect of the invention, the manufacturing system is automated.

In yet another aspect of the invention, at least one device can be in more than one room.

In yet another aspect of the invention, the manufacturing system further includes at least one disposable bag that can be used to dispose of at least one device, tubing or connector.

Example 1

A manufacturing facility that has completely closed, fully disposable, and scalable production systems having integrated disposables designed for each aspect of product production. The equipment is connected to each other as shown in FIG. 1 in the following order: input cells (1), inoculum expansion equipment (2), production stage bioreactor equipment (3), primary recovery stage equipment (4), equipment for the capture step (5), ultrafiltration and diafiltration equipment (6), polishing membranes (7), equipment for polishing using cation exchange (8), virus reduction filtration equipment (9), ultrafiltration and diafiltration equipment (10), and automated bulk fill equipment (11).

Product is made by adding the input cells at Step 1. The equipment in Step 1 opens the containers that contain the input cells. The contents are moved to the inoculum expansion equipment (2) through tubes that connect these pieces of equipment. Then, the contents are moved to the production stage bioreactor equipment (3). The contents are then transferred to the primary recovery stage equipment (4). After which, the contents are sent to the equipment for the capture (5). Once captured, the contents are moved to the ultrafiltration and diafiltration equipment (6). The contents are next sent to the polishing membranes (7) and the equipment for polishing using cation exchange (8). Then the contents are moved to the virus reduction filtration equipment (9). Next, the contents are moved to the ultrafiltration and diafiltration equipment (10). Then, the contents are moved to the automated bulk fill equipment (11). The ultrafiltration and diafiltration equipment (10) and the automated bulk fill equipment (11) can be in a separate room. Ideally, there are connectors that can move the contents directly, but it is also contemplated by this invention that the contents will be transferred by other means at this point.

Example 2

A manufacturing facility that is a partly closed, fully disposable, and scalable production systems having integrated disposables designed for each aspect of product production. The equipment is connected to each other as shown in FIG. 1 in the following order: input cells (1), inoculum expansion equipment (2), production stage bioreactor equipment (3), primary recovery stage equipment (4), equipment for the capture step (5), ultrafiltration and diafiltration equipment (6), polishing membranes (7), equipment for polishing using cation exchange (8), virus reduction filtration equipment (9), ultrafiltration and diafiltration equipment (10), and automated bulk fill equipment (11).

Product is made by adding the input cells at Step 1. The equipment in Step 1 opens the containers that contain the input cells. The contents are moved to the inoculum expansion equipment (2) through tubes that connect these pieces of equipment. Then, the contents are moved to the production stage bioreactor equipment (3). The contents are then transferred to the primary recovery stage equipment (4). After which, the contents are sent to the equipment for the capture (5). Once captured, the contents are moved to the ultrafiltration and diafiltration equipment (6). The contents are next sent to the polishing membranes (7) and the equipment for polishing using cation exchange (8). Then the contents are moved to the virus reduction filtration equipment (9). Next, the contents are moved to the ultrafiltration and diafiltration equipment (10). Then, the contents are moved to the automated bulk fill equipment (11). The ultrafiltration and diafiltration equipment (10) and the automated bulk fill equipment (11) can be in a separate room. Ideally, there are connectors that can move the contents directly, but it is also contemplated by this invention that the contents will be transferred by other means at this point.

Example 3

A manufacturing facility that is an only partly disposable and scalable production system having integrated disposables designed for each aspect of product production. The equipment is connected to each other as shown in FIG. 1 in the following order: input cells (1), inoculum expansion equipment (2), production stage bioreactor equipment (3), primary recovery stage equipment (4), equipment for the capture step (5), ultrafiltration and diafiltration equipment (6), polishing membranes (7), equipment for polishing using cation exchange (8), virus reduction filtration equipment (9), ultrafiltration and diafiltration equipment (10), and automated bulk fill equipment (11).

Product is made by adding the input cells at Step 1. The equipment in Step 1 opens the containers that contain the input cells. The contents are moved to the inoculum expansion equipment (2) through tubes that connect these pieces of equipment. Then, the contents are moved to the production stage bioreactor equipment (3). The contents are then transferred to the primary recovery stage equipment (4). After which, the contents are sent to the equipment for the capture (5). Once captured, the contents are moved to the ultrafiltration and diafiltration equipment (6). The contents are next sent to the polishing membranes (7) and the equipment for polishing using cation exchange (8). Then the contents are moved to the virus reduction filtration equipment (9). Next, the contents are moved to the ultrafiltration and diafiltration equipment (10). Then, the contents are moved to the automated bulk fill equipment (11). The ultrafiltration and diafiltration equipment (10) and the automated bulk fill equipment (11) can be in a separate room. Ideally, there are connectors that can move the contents directly, but it is also contemplated by this invention that the contents will be transferred by other means at this point.

Example 4

A manufacturing facility that has completely closed, fully disposable, and scalable production systems having integrated disposables designed for each aspect of product production. The equipment is connected to each other as shown in FIG. 2 in the following order: input cells (1), inoculum expansion equipment (2), production stage perfusion equipment (12), equipment for volume exchange (13), continuous purification equipment (14), virus reduction filtration equipment (9), ultrafiltration and diafiltration equipment (10), and automated bulk fill equipment (11).

Product is made by adding the input cells at Step 1. The equipment in Step 1 opens the containers that contain the input cells. The contents are moved to the inoculum expansion equipment (2) through tubes that connect these pieces of equipment. Then, the contents are moved to production stage perfusion equipment (12). After that, the contents are transferred to the equipment for volume exchange (13). Then, the contents are sent to the continuous purification equipment (14). Then the contents are moved to the virus reduction filtration equipment (9). Next, the contents are moved to the ultrafiltration and diafiltration equipment (10). Then, the contents are moved to the automated bulk fill equipment (11). The ultrafiltration and diafiltration equipment (10) and the automated bulk fill equipment (11) can be in a separate room. Ideally, there are connectors that can move the contents directly, but it is also contemplated by this invention that the contents will be transferred by other means at this point.

Example 5

A manufacturing facility that is a partly closed, fully disposable, and scalable production systems having integrated disposables designed for each aspect of product production. The equipment is connected to each other as shown in FIG. 2 in the following order: input cells (1), inoculum expansion equipment (2), production stage perfusion equipment (12), equipment for volume exchange (13), continuous purification equipment (14), virus reduction filtration equipment (9), ultrafiltration and diafiltration equipment (10), and automated bulk fill equipment (11).

Product is made by adding the input cells at Step 1. The equipment in Step 1 opens the containers that contain the input cells. The contents are moved to the inoculum expansion equipment (2) through tubes that connect these pieces of equipment. Then, the contents are moved to production stage perfusion equipment (12). After that, the contents are transferred to the equipment for volume exchange (13). Then, the contents are sent to the continuous purification equipment (14). Then the contents are moved to the virus reduction filtration equipment (9). Next, the contents are moved to the ultrafiltration and diafiltration equipment (10). Then, the contents are moved to the automated bulk fill equipment (11). The ultrafiltration and diafiltration equipment (10) and the automated bulk fill equipment (11) can be in a separate room. Ideally, there are connectors that can move the contents directly, but it is also contemplated by this invention that the contents will be transferred by other means at this point.

Example 6

A manufacturing facility that is an only partly disposable and scalable production system having integrated disposables designed for each aspect of product production.

The equipment is connected to each other as shown in FIG. 2 in the following order: input cells (1), inoculum expansion equipment (2), production stage perfusion equipment (12), equipment for volume exchange (13), continuous purification equipment (14), virus reduction filtration equipment (9), ultrafiltration and diafiltration equipment (10), and automated bulk fill equipment (11).

Product is made by adding the input cells at Step 1. The equipment in Step 1 opens the containers that contain the input cells. The contents are moved to the inoculum expansion equipment (2) through tubes that connect these pieces of equipment. Then, the contents are moved to production stage perfusion equipment (12). After that, the contents are transferred to the equipment for volume exchange (13). Then, the contents are sent to the continuous purification equipment (14). Then the contents are moved to the virus reduction filtration equipment (9). Next, the contents are moved to the ultrafiltration and diafiltration equipment (10). Then, the contents are moved to the automated bulk fill equipment (11). The ultrafiltration and diafiltration equipment (10) and the automated bulk fill equipment (11) can be in a separate room. Ideally, there are connectors that can move the contents directly, but it is also contemplated by this invention that the contents will be transferred by other means at this point.

Example 7

A manufacturing facility that has completely closed, fully disposable, and scalable production systems having integrated disposables designed for each aspect of product production. The equipment is connected to each other as shown in FIG. 3 in the following order input cells (1), inoculum expansion equipment (2), production stage bioreactor equipment (3), primary recovery stage equipment (4), equipment for volume exchange (13), continuous purification equipment (14), virus reduction filtration equipment (9), ultrafiltration and diafiltration equipment (10), and automated bulk fill equipment (11).

Product is made by adding the input cells at Step 1. The equipment in Step 1 opens the containers that contain the input cells. The contents are moved to the inoculum expansion equipment (2) through tubes that connect these pieces of equipment. Then, the contents are moved to the production stage bioreactor equipment (3). The contents are then transferred to the primary recovery stage equipment (4). After which, the contents are sent to equipment for volume exchange (13), continuous purification equipment (14), virus reduction filtration equipment (9), ultrafiltration and diafiltration equipment (10), and automated bulk fill equipment (11).

Example 8

A manufacturing facility that is a partly closed, fully disposable, and scalable production systems having integrated disposables designed for each aspect of product production. The equipment is connected to each other as shown in FIG. 3 in the following order: input cells (1), inoculum expansion equipment (2), production stage bioreactor equipment (3), primary recovery stage equipment (4), equipment for volume exchange (13), continuous purification equipment (14), virus reduction filtration equipment (9), ultrafiltration and diafiltration equipment (10), and automated bulk fill equipment (11).

Product is made by adding the input cells at Step 1. The equipment in Step 1 opens the containers that contain the input cells. The contents are moved to the inoculum expansion equipment (2) through tubes that connect these pieces of equipment. Then, the contents are moved to the production stage bioreactor equipment (3). The contents are then transferred to the primary recovery stage equipment (4). After which, the contents are sent to equipment for volume exchange (13), continuous purification equipment (14), virus reduction filtration equipment (9), ultrafiltration and diafiltration equipment (10), and automated bulk fill equipment (11).

Example 8

A manufacturing facility that is an only partly disposable and scalable production system having integrated disposables designed for each aspect of product production. The equipment is connected to each other as shown in FIG. 3 in the following order: input cells (1), inoculum expansion equipment (2), production stage bioreactor equipment (3), primary recovery stage equipment (4), equipment for volume exchange (13), continuous purification equipment (14), virus reduction filtration equipment (9), ultrafiltration and diafiltration equipment (10), and automated bulk fill equipment (11).

Product is made by adding the input cells at Step 1. The equipment in Step 1 opens the containers that contain the input cells. The contents are moved to the inoculum expansion equipment (2) through tubes that connect these pieces of equipment. Then, the contents are moved to the production stage bioreactor equipment (3). The contents are then transferred to the primary recovery stage equipment (4). After which, the contents are sent to equipment for volume exchange (13), continuous purification equipment (14), virus reduction filtration equipment (9), ultrafiltration and diafiltration equipment (10), and automated bulk fill equipment (11).

It should be recognized that the one or more examples in the disclosure are non-limiting examples and that the present invention is intended to encompass variations and equivalents of these examples.

The invention claimed is:

1. A manufacturing system for biopharmaceuticals comprising:
   at least one inputting device directly connected to at least one inoculum expansion device through at least one piece of tubing and a connector that does not include a shake flask incubation device, wherein the direct connection contains a sensor that controls a transfer of a material from the at least one inputting device to the at least one inoculum expansion device;
   said at least one inoculum expansion device is connected to at least one production stage bioreactor device through at least one piece of tubing and a connector;
   said at least one production stage bioreactor device is connected to at least one primary recovery device through at least one piece of tubing and a connector;
   said at least one primary recovery device is directly connected to at least one capturing device by at least one piece of tubing and a connector;
   said at least one capturing device is connected to at least one ultrafiltration and diafiltration device through at least one piece of tubing and a connector;
   said at least one ultrafiltration and diafiltration device connected to the capturing device is connected to at least one polishing membranes device through at least one piece of tubing and a connector;
   said at least one polishing membranes device is connected to at least one polishing using cation exchange device through at least one piece of tubing and a connector;
   said at least one polishing using cation exchange device is connected to at least one virus reduction filtration device through at least one piece of tubing and a connector; and
   said at least one virus reduction filtration device is connected to at least one ultrafiltration and diafiltration device through at least one piece of tubing and a connector;
   said at least one ultrafiltration and diafiltration device connected to the virus reduction filtration device is connected to at least one automated bulk fill device through at least one piece of tubing and a connector,
   wherein the device can be from at least two different manufacturers and wherein the system is configured to be switchable for difference processes.

2. The manufacturing system of claim 1, wherein at least one device is not made for single-use.

3. The manufacturing system of claim 1, wherein the system is operated as a closed system.

4. The manufacturing system of claim 1, further comprising at least one sensor capable of controlling flow of material between two devices.

5. The manufacturing system of claim 1, wherein the system is automated.

6. The manufacturing system of claim 1, wherein at least one device can be in more than one room.

7. The manufacturing system of claim 1, further comprising at least one disposable bag that can be used to dispose of at least one device, tubing or connector.

8. A method of making biopharmaceuticals comprising:
   directly connecting at least one inputting device to at least one inoculum expansion device using at least one piece of tubing and a connector such that material can directly pass from the inputting device to the inoculum expansion device without a shake flask incubation step, wherein the direct connection contains a sensor that controls passing of material from the at least one inputting device to the at least one inoculum expansion device;
   connecting said at least one inoculum expansion device to at least one production stage bioreactor device using at least one piece of tubing and a connector such that material can pass from the inoculum expansion device to the production stage bioreactor device;
   connecting said at least one production stage bioreactor device to at least one primary recovery device using at least one piece of tubing and a connector such that material can pass from the production stage bioreactor device to the primary recovery device;
   connecting said at least one primary recovery device directly, to at least one capturing device using at least one piece of tubing and a connector such that material can pass from the primary recovery device to the capturing device;

connecting said at least one capturing device to at least one ultrafiltration and diafiltration device using at least one piece of tubing and a connector such that material can pass from the capturing device to the ultrafiltration and diafiltration device;

connecting said at least one ultrafiltration and diafiltration device to at least one polishing membranes device using at least one piece of tubing and a connector such that material can pass from the ultrafiltration and diafiltration device to the polishing membrane device;

connecting said at least one polishing membranes device to at least one polishing using cation exchange device using at least one piece of tubing and a connector such that material can pass from the polishing membranes device to the polishing using cation exchange device; and connecting said at least one polishing using cation exchange device to at least one virus reduction filtration device using at least one piece of tubing and a connector such that material can pass from the polishing using cation exchange device to the virus reduction filtration device;

wherein the device can be from at least two different manufacturers and wherein the system is configured to be switchable for difference processes.

9. The method of claim 8, further comprising:

connecting said at least one virus reduction filtration device to at least one ultrafiltration and diafiltration device such that material can pass from the virus reduction filtration device to the ultrafiltration and diafiltration device; and connecting said at least one ultrafiltration and diafiltration device to at least one automated bulk fill device such that material can pass from the ultrafiltration and diafiltration device to the automated bulk fill device.

10. The method of claim 8, wherein the method is automated.

11. The method of claim 9, wherein the method is automated.

12. A manufacturing system for biopharmaceuticals comprising:

at least one inputting device directly connected to at least one inoculum expansion device through at least one piece of tubing and a connector that does not include a shake flask incubation device, wherein the direct connection contains a sensor that controls a transfer of a material from the at least one inputting device to the at least one inoculum expansion device;

said at least one inoculum expansion device is connected to at least one production stage perfusion device through at least one piece of tubing and a connector;

said at least one production stage perfusion device is connected directly to at least one volume exchange device through at least one piece of tubing and a connector;

said at least one volume exchange device is connected to at least one continuous filtration device through at least one piece of tubing and a connector;

said at least one continuous filtration device is connected to at least one virus reduction filtration device through at least one piece of tubing and a connector;

said at least one virus reduction filtration device is connected to at least one ultrafiltration and diafiltration device through at least one piece of tubing and a connector; and said at least one ultrafiltration and diafiltration device connected to the virus reduction filtration device is connected to at least one automated bulk fill device through at least one piece of tubing and a connector, wherein the device can be from at least two different manufacturers and wherein the system is configured to be switchable for difference processes.

13. The manufacturing system of claim 12, wherein at least one device is not made for single-use.

14. The manufacturing system of claim 12, wherein the system is operated as a closed system.

15. The manufacturing system of claim 12, further comprising at least one sensor capable of controlling flow of material between two devices.

16. The manufacturing system of claim 12, wherein the system is automated.

17. The manufacturing system of claim 12, wherein at least one device can be in more than one room.

18. The manufacturing system of claim 12, further comprising at least one disposable bag that can be used to dispose of at least one device, tubing or connector.

19. A method of making biopharmaceuticals comprising:

directly connecting at least one inputting device to at least one inoculum expansion device using at least one piece of tubing and a connector such that material can pass directly from the inputting device to the inoculum expansion device without a shake flask incubation step, wherein the direct connection contains a sensor that controls passing of material from the at least one inputting device to the at least one inoculum expansion device;

connecting said at least one inoculum expansion device to at least one production stage perfusion device using at least one piece of tubing and a connector such that material can pass from the inoculum expansion device to the production stage perfusion device;

connecting said at least one production stage perfusion device directly to at least one volume exchange device using at least one piece of tubing and a connector such that material can pass from the production stage perfusion device to the volume exchange device;

connecting said at least one volume exchange device to at least one continuous purification device using at least one piece of tubing and a connector such that material can pass from the volume exchange device to the continuous purification device;

connecting said at least one continuous purification device to at least one virus reduction filtration device using at least one piece of tubing and a connector such that material can pass from the continuous purification device to the virus reduction filtration device;

connecting said at least one virus reduction filtration device to at least one ultrafiltration and diafiltration device using at least one piece of tubing and a connector such that material can pass from the virus reduction filtration device to the ultrafiltration and diafiltration device; and connecting said at least one ultrafiltration and diafiltration device to at least one automated bulk fill device using at least one piece of tubing and a connector such that material can pass from the ultrafiltration and diafiltration device to the automated bulk fill device.

20. A manufacturing system for biopharmaceuticals comprising:

at least one inputting device directly connected to at least one inoculum expansion device through at least one piece of tubing and a connector that does not include a shake flask incubation device, wherein the direct connection contains a sensor that controls a transfer of a material from the at least one inputting device to the at least one inoculum expansion device;

said at least one inoculum expansion device is connected to at least one production stage bioreactor device through at least one piece of tubing and a connector;

said at least one production stage bioreactor device is connected to at least one primary recovery device through at least one piece of tubing and a connector;

said at least one primary recovery device is directly connected to at least one volume exchange device through at least one piece of tubing and a connector;

said at least one volume exchange device is connected to at least one continuous purification device through at least one piece of tubing and a connector;

said at least one continuous purification device is connected to at least one virus reduction filtration device through at least one piece of tubing and a connector;

said at least one virus reduction filtration device is connected to at least one ultrafiltration and diafiltration device through at least one piece of tubing and a connector; and said at least one ultrafiltration and diafiltration device connected to the virus reduction filtration device is connected to at least one automated bulk fill device through at least one piece of tubing and a connector, wherein the device can be from at least two different manufacturers and wherein the system is configured to be switchable for difference processes.

21. The manufacturing system of claim 20, wherein at least one device is not made for single-use.

22. The manufacturing system of claim 20, wherein the system is operated as a closed system.

23. The manufacturing system of claim 20, further comprising at least one sensor capable of controlling flow of material between two devices.

24. The manufacturing system of claim 20, wherein the system is automated.

25. The manufacturing system of claim 20, wherein at least one device can be in more than one room.

26. The manufacturing system of claim 20, further comprising at least one disposable bag that can be used to dispose of at least one of device, tubing or connector.

27. A method of making biopharmaceuticals comprising:

directly connecting at least one inputting device to at least one inoculum expansion device using at least one piece of tubing and a connector such that material can directly pass from the inputting device to the inoculum expansion device without a shake flask incubation step, wherein the direct connection contains a sensor that controls passing of material from the at least one inputting device to the at least one inoculum expansion device;

connecting said at least one inoculum expansion device to at least one production stage bioreactor device using at least one piece of tubing and a connector such that material can pass from the inoculum expansion device to the production stage bioreactor device;

connecting said at least one production stage bioreactor device to at least one primary recovery device using at least one piece of tubing and a connector such that material can pass from the production stage bioreactor device to the primary recovery device;

directly connecting said at least one primary recovery device to at least one volume exchange device using at least one piece of tubing and a connector such that material can pass from the primary recovery device to the volume exchange device;

connecting said at least one volume exchange device to at least one continuous purification device using at least one piece of tubing and a connector such that material can pass from the volume exchange device to the continuous purification device;

connecting said at least one continuous purification device to at least one virus reduction filtration device using at least one piece of tubing and a connector such that material can pass from the continuous purification device to the virus reduction filtration device;

connecting said at least one virus reduction filtration device to at least one ultrafiltration and diafiltration device using at least one piece of tubing and a connector such that material can pass from the virus reduction filtration device to the ultrafiltration and diafiltration device; and connecting said at least one ultrafiltration and diafiltration device to at least one automated bulk fill device using at least one piece of tubing and a connector such that material can pass from the ultrafiltration and diafiltration device to the automated bulk fill device.

28. A manufacturing system for biopharmaceuticals comprising:

at least one inputting device directly connected to at least one inoculum expansion device through at least one piece of tubing and a connector that does not include a shake flask incubation device, wherein the direct connection contains a sensor that controls a transfer of a material from the at least one inputting device to the at least one inoculum expansion device;

said at least one inoculum expansion device is connected to at least one production stage perfusion device through at least one piece of tubing and a connector;

said at least one production stage perfusion device is directly connected to at least one volume exchange device through at least one piece of tubing and a connector;

said at least one volume exchange device is connected to at least one continuous purification device through at least one piece of tubing and a connector;

said at least one continuous purification device is connected to at least one virus reduction filtration device through at least one piece of tubing and a connector;

said at least one virus reduction filtration device is connected to at least one ultrafiltration and diafiltration device through at least one piece of tubing and a connector; and said at least one ultrafiltration and diafiltration device is connected to at least one automated bulk fill device through at least one piece of tubing and a connector.

29. The manufacturing system of claim 28, wherein the device can be from at least two different manufacturers.

30. The manufacturing system of claim 28, wherein at least one device is not made for single-use.

31. The manufacturing system of claim 28, wherein there the system operated as a closed system.

32. The manufacturing system of claim 28, further comprising at least one sensor capable of controlling flow of material between two devices.

33. The manufacturing system of claim 28, wherein the system is automated.

34. The manufacturing system of claim 28, wherein at least one device can be in more than one room.

35. The manufacturing system of claim 28, further comprising at least one disposable bag that can be used to dispose of at least one device, tubing or connector.

36. A method for manufacturing biopharmaceuticals comprising:
  directly connecting at least one inputting device to at least one inoculum expansion device using at least one piece of tubing and a connector such that material can directly pass from the inputting device to the inoculum expansion device without a shake flask incubation step, wherein the direct connection contains a sensor that controls passing of material from the at least one inputting device to the at least one inoculum expansion device;
  connecting said at least one inoculum expansion device to at least one production stage bioreactor device using at least one piece of tubing and a connector such that material can pass from the inoculum expansion device to the production stage bioreactor device;
  connecting said at least one production stage bioreactor device to at least one primary recovery device using at least one piece of tubing and a connector such that material can pass from the production stage bioreactor device to the primary recovery device;
  directly connecting said at least one primary recovery device to at least one volume exchange device using at least one piece of tubing and a connector such that material can pass from the primary recovery device to the volume exchange device;
  connecting said at least one volume exchange device to at least one continuous purification device using at least one piece of tubing and a connector such that material can pass from the volume exchange device to the continuous purification device;
  connecting said at least one continuous purification device to at least one virus reduction filtration device using at least one piece of tubing and a connector such that material can pass from the continuous purification device to the virus reduction filtration device;
  connecting said at least one virus reduction filtration device to at least one ultrafiltration and diafiltration device using at least one piece of tubing and a connector such that material can pass from the virus reduction filtration device to the ultrafiltration and diafiltration device; and
  connecting said at least one ultrafiltration and diafiltration device to at least one automated bulk fill device using at least one piece of tubing and a connector such that material can pass from the ultrafiltration and diafiltration device to the automated bulk fill device.

37. A method to manufacture a biopharmaceutical product comprising:
  inserting a material into an inoculum device for processing;
  transferring the material from the inoculum device to an inoculum expansion device for further processing, wherein inoculum device is directly connected to the inoculum expansion device without a shake flask incubation step, wherein the direct connection contains a sensor that controls the transfer of the material from the at least one inoculum device to the at least one inoculum expansion device;
  then transferring the material from the inoculum expansion device to a production stage bioreactor device for further processing;
  then transferring the material from the production stage bioreactor device to a primary recovery device for further processing;
  then transferring the material directly from the primary recovery device to a capturing device for further processing;
  then transferring the material from the capturing device to an ultrafiltration and diafiltration device for further processing;
  then transferring the material from the ultrafiltration and diafiltration device to a polishing membrane device for further processing;
  then transferring the material from the polishing membrane device to a polishing using cation exchange device for further processing;
  then transferring the material from the polishing using cation exchange device to a virus reduction filtration device for further processing;
  then transferring the material from the virus reduction filtration device to an ultrafiltration and diafiltration device for further processing; and
  then transferring the material from the ultrafiltration and diafiltration device to an automated bulk fill device to obtain the biopharmaceutical product.

38. A method to manufacture a biopharmaceutical product comprising:
  inserting a material into an inoculum device for processing;
  transferring the material from the inoculum device to an inoculum expansion device for further processing, wherein inoculum device is directly connected to the inoculum expansion device without a shake flask incubation step, wherein the direct connection contains a sensor that controls the transfer of the material from the at least one inoculum device to the at least one inoculum expansion device;
  then transferring the material from the inoculum expansion device to a production stage perfusion device for further processing;
  then directly transferring the material from the production stage perfusion device to a volume exchange device for further processing;
  then transferring the material from the volume exchange device to a continuous filtration device for further processing;
  then transferring the material from the continuous filtration device to a virus reduction filtration device for further processing;
  then transferring the material from the virus reduction filtration device to an ultrafiltration and diafiltration device for further processing; and
  then transferring the material from the ultrafiltration and diafiltration device to an automated bulk fill device to obtain the biopharmaceutical product.

39. A method to manufacture a biopharmaceutical product comprising:
  inserting a material into an inoculum device for processing;
  transferring the material from the inoculum device to an inoculum expansion device for further processing, wherein inoculum device is directly connected to the inoculum expansion device without a shake flask incubation step, wherein the direct connection contains a sensor that controls the transfer of the material from the at least one inoculum device to the at least one inoculum expansion device;
  then transferring the material from the inoculum expansion device to a production stage bioreactor device for further processing;

then directly transferring the material from the production stage bioreactor device to a primary recovery device for further processing;
then transferring the material from the primary recovery device to a volume exchange device for further processing;
then transferring the material from the volume exchange device to a continuous purification device for further processing;
then transferring the material from the continuous purification device to a virus reduction filtration device for further processing;
then transferring the material from the virus reduction filtration device to an ultrafiltration and diafiltration device for further processing; and
then transferring the material from the ultrafiltration and diafiltration device to an automated bulk fill device to obtain the biopharmaceutical product.

40. A method to manufacture a biopharmaceutical product comprising:
inserting a material into an inoculum device for processing;
transferring the material from the inoculum device to an inoculum expansion device for further processing, wherein inoculum device is directly connected to the inoculum expansion device without a shake flask incubation step, wherein the direct connection contains a sensor that controls the transfer of the material from the at least one inoculum device to the at least one inoculum expansion device;
then transferring the material from the inoculum expansion device to a production stage perfusion device for further processing;
then directly transferring the material from the production stage perfusion device to a volume exchange device for further processing;
then transferring the material from the volume exchange device to a continuous purification device for further processing;
then transferring the material from the continuous purification device to a virus reduction filtration device for further processing;
then transferring the material from the virus reduction filtration device to an ultrafiltration and diafiltration device for further processing; and
then transferring the material from the ultrafiltration and diafiltration device to an automated bulk fill device to obtain the biopharmaceutical product.

* * * * *